United States Patent
Barrientos

(10) Patent No.: US 7,517,341 B2
(45) Date of Patent: *Apr. 14, 2009

(54) URINE COLLECTION SUSPENSION AND SAFETY SYSTEM

(75) Inventor: Joel K. Barrientos, Chicago, IL (US)

(73) Assignee: Joel Kwan Barrientos, Centralia, IL (US)

(*) Notice: Subject to any disclaimer, the term of this patent is extended or adjusted under 35 U.S.C. 154(b) by 65 days.

This patent is subject to a terminal disclaimer.

(21) Appl. No.: 11/368,940

(22) Filed: Mar. 6, 2006

(65) Prior Publication Data

US 2007/0208314 A1    Sep. 6, 2007

(51) Int. Cl.
*A61F 5/44* (2006.01)

(52) U.S. Cl. ............ 604/353; 604/343; 604/344; 604/345; 604/349; 604/351; 604/264; 604/523; 604/327; 604/317; 604/179; 128/876

(58) Field of Classification Search ............ 604/353, 604/343–345, 349, 351, 179, 264, 523, 327, 604/317; 128/876
See application file for complete search history.

(56) References Cited

U.S. PATENT DOCUMENTS

| | | | | |
|---|---|---|---|---|
| 2,133,130 A | | 10/1938 | Buchstein | 128/349 |
| 2,476,375 A | * | 7/1949 | Kent | 604/353 |
| 3,726,280 A | * | 4/1973 | Lacount | 604/179 |
| 3,897,785 A | * | 8/1975 | Barto, Jr. | 604/327 |
| 4,057,066 A | * | 11/1977 | Taylor | 604/180 |
| 4,073,295 A | | 2/1978 | Laufbahn | 128/295 |
| 4,319,573 A | * | 3/1982 | Whitlock | 604/328 |
| 4,726,716 A | * | 2/1988 | McGuire | 604/180 |
| 5,664,581 A | * | 9/1997 | Ashley | 128/876 |
| D395,356 S | * | 6/1998 | Tang | D3/327 |
| 6,032,289 A | * | 3/2000 | Villapiano | 2/102 |
| 6,096,013 A | * | 8/2000 | Hakky et al. | 604/349 |
| 6,645,185 B2 | * | 11/2003 | Bird et al. | 604/345 |
| 2004/0162535 A1 | * | 8/2004 | Preston et al. | 604/329 |
| 2007/0179462 A1 | * | 8/2007 | Barrientos | 604/353 |

* cited by examiner

*Primary Examiner*—Tatyana Zalukaeva
*Assistant Examiner*—Ginger T Chapman
(74) *Attorney, Agent, or Firm*—Harness, Dickey & Pierce, P.L.C.

(57) ABSTRACT

A urine collection system includes a urine collection device and a support system. The urine collection device includes a catheter and collection component. The suspension system includes a waist band, an extension strap depending from the waist band, and a thigh band attached to the strap. A pair of securing straps is provided for securing the urine collection tubing. A fastener is provided on the extension strap for securing the catheter and for resisting movement of the catheter due to relative pulling of collection tubing or a collection bag. The catheter further includes a branch, which, along with the fastener, resists the downward motion of the catheter.

12 Claims, 4 Drawing Sheets

URINE COLLECTION SUSPENSION AND SAFETY SYSTEM

FIELD OF THE INVENTION

The present invention relates generally to urine collection devices, and more particularly to urine collection devices with wearable supports for incontinent patients.

BACKGROUND

A conventional urine collection device includes an external or internal catheter (such as a Foley catheter) communicating with the subject's urethra, and a urine bag connected to the catheter for collecting urine. To enhance the subject's mobility the urine bag can be secured to one of the patient's thighs. The urine collection device is thus hidden under the clothing of the patient so that the patient can engage in daily activities without embarrassment.

Conventional urine collection devices, however, can cause discomfort to the patient. If not properly supported, the urine bag tends to swing back and forth across the patient's thigh as the patient moves, impeding free movement of the patient. Moreover, as more urine is collected, the weight of urine bag can cause it to slide, applying a pulling force that is at best uncomfortable for the subject, and in the case of an internal catheter, can forcibly pull the catheter from the subject's urethra, causing severe trauma and pain to the subject.

Attempts have been made to provide more secure support for urine collection device discomfort and embarrassment, and in many cases pain and trauma are still common side effects of using a mobile urine collection system.

SUMMARY

Embodiments of the present invention provide for more secure support for urine collection system with reduced risk to the user. In one preferred form, a urine bag suspension system for carrying a urine collection device is provided. The urine bag suspension system includes a waist band, a urine bag support suspended from the waist band for carrying a urine bag of the urine collection device, and a fastener. The fastener is disposed at the urine bag support for engaging the catheter of the urine collection device to resist pulling it from communication with the subject's urethra.

In another preferred form, a urine bag suspension system for carrying a urine collection device is provided. The urine collection device includes a catheter and a urine bag. The catheter has an engaging end removably engaging the urine bag. The urine bag suspension system includes a waist band, an extension strap suspended from the waist band, and a bag carrier for carrying the urine bag. The extension strap is substantially vertically suspended from the waist band and is connected to about the midway of an upper edge of the bag carrier. The bag carrier includes a pair of securing straps.

In still another preferred form, a wearable support for a urine collection system comprising a catheter and a length of tubing for connection to a collection device is provided. The support comprises a waist band adapted to be worn around the user's waist, a strap depending from the waist band, and a thigh band attached to the strap, adapted to be worn around the user's thigh. The support further comprises at least one fastener on the thigh band for engaging and supporting the length of tubing, and at least one fastener on the strap for engaging the catheter to resist pulling of the tubing, via the fasteners on the thigh band.

Various embodiments of the invention provide more secure support for the urine bags in urine collection systems to resist movement of the bag and attendant discomfort to the subject. Various embodiments of the invention also engage the catheter to resist movement of the catheter and resulting discomfort and trauma to the subject. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings of preferred embodiments thereof, wherein.

Corresponding reference numerals indicate corresponding parts throughout the several views of the drawings.

DETAILED DESCRIPTION

The structure of a urine collection system in accordance with the present disclosure is now described in greater detail. The following description of the illustrated example is merely exemplary in nature and is in no way intended to limit the invention, its application, or uses.

Figure 1:
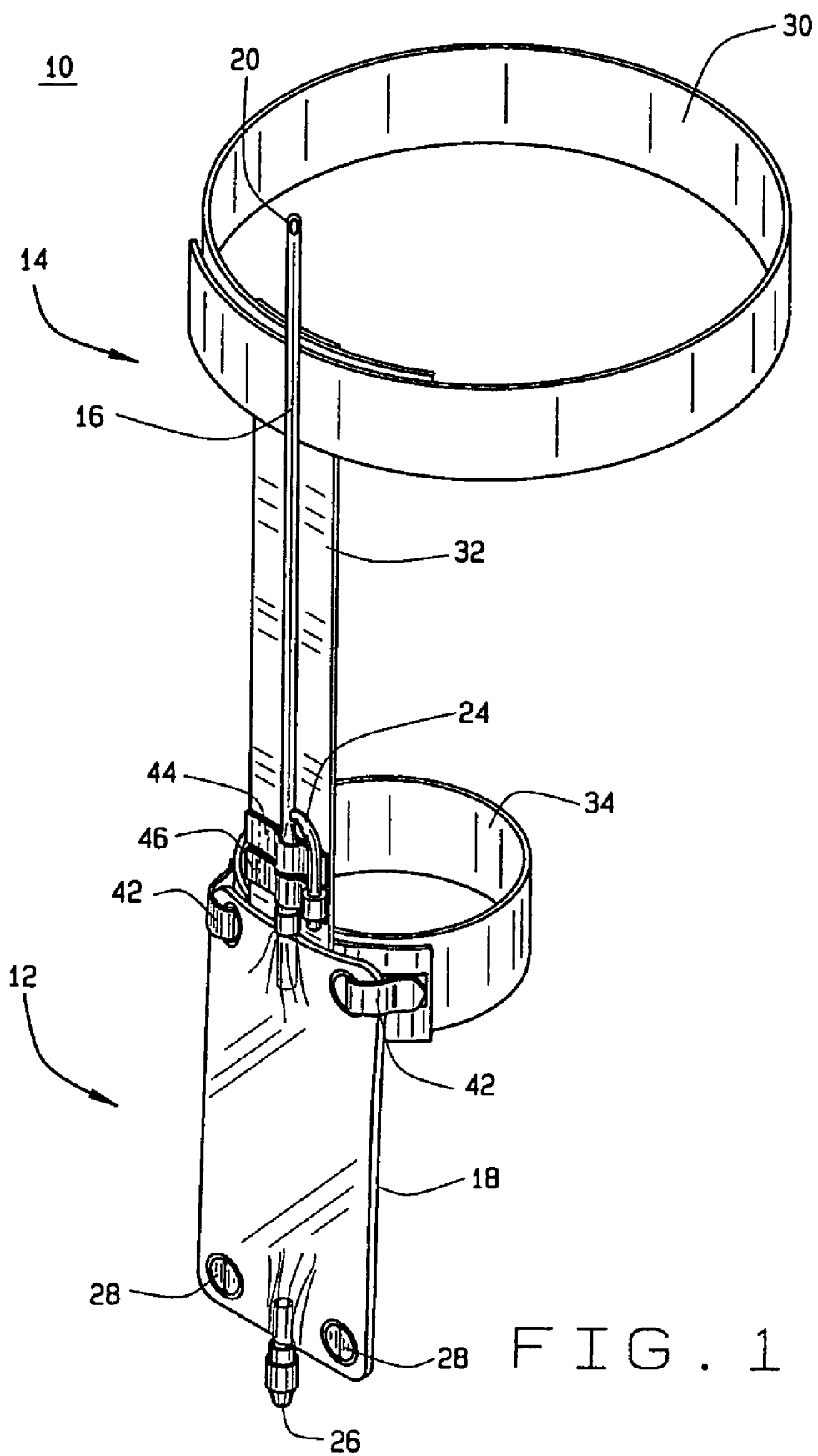
FIG. 1 is a perspective view of one embodiment of a urine collection system in accordance with the teachings of the present disclosure.
Figure 2:
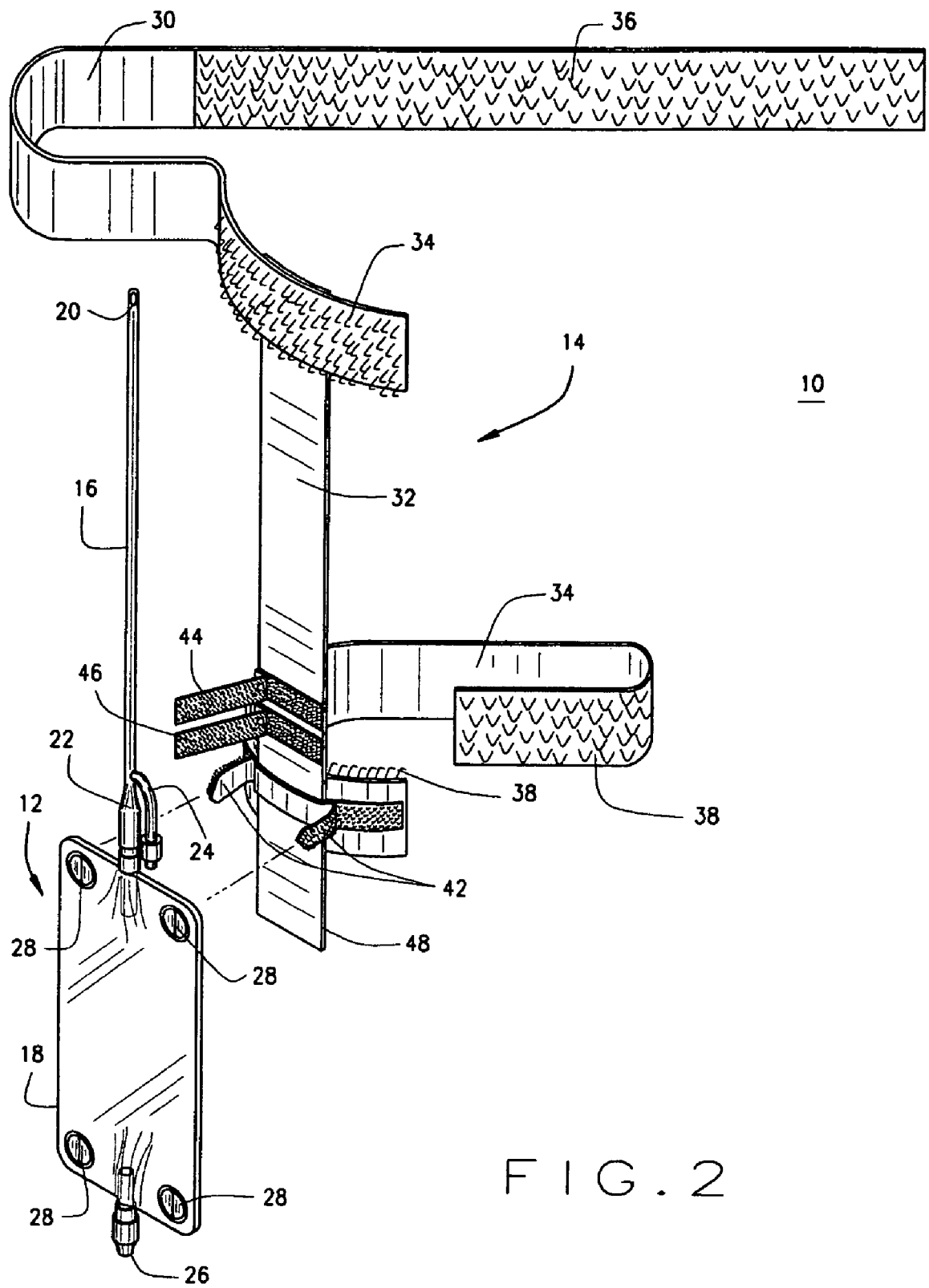
FIG. 2 is a perspective view of the urine collection system of FIG. 1, wherein the urine collection device is disassembled from a wearable suspension system therefore.

Referring to FIGS. 1 and 2, one embodiment of a urine collection system in accordance with the teachings of the present disclosure is illustrated and generally indicated by reference numeral 10. The urine collection system 10 includes a urine collection device 12 and a wearable support or a wearable suspension system 14. The urine collection device 12 includes a catheter 16 and a urine bag 18. The catheter 16 has an inlet end 20 for communicating with the urethra of the subject, and an outlet end 22 for engaging the urine bag 18.

The catheter 16 can be a Foley catheter, which is adapted to be inserted into the urethra of the patient, or a Texas catheter, which is to be connected to the penis of a male patient via a condom-like envelope, or any other type of internal or external urine collection catheter. In any case, the catheter 16 usually includes a branch 24 adjacent to the outlet end 22, the function of which will be described later.

The urine bag 18 has a discharge outlet 26 at the opposite end of the bag from the connection to the outlet end 22 of the catheter 16 for emptying the urine bag 24. In most applications the bag 18 is mounted generally vertically, with the connection to the outlet end 22 of the catheter at the upper end of the bag, and the discharge outlet 26 at the lower end. The urine bag 18 preferably has a generally rectangular shape with four corners and four eyelets 28, one at each of its four corners for mounting the bag.

The suspension system 14 is used to support and carry the urine collection device 12 on the subject, and includes a waist band 30, an extension strap 32 depending from the waist band 30, and a thigh band 34 attached adjacent the free end of the extension strap 32. The waist band 30 could be a continuous loop, but it is preferably in the form of a belt for encircling the entire waist of the subject. The waist band 30 could also be in the form of a strip to be attached to a piece of clothing around the subject's waist without completely encircling the subject's waist. In either case, the waist band 30 can be provided with a fastener 36 to make it easy for the subject to put the suspension system 14 on, and take it off. In the illustrated example, the fastener 36 includes an elongated band with mating fastener elements. The mating fastening elements are preferably mating patches of a hook-and-loop style fastener, such as Velcro® fastener, to allow easy attachment and detachment. However, any conventional fasteners, such as buckles, buttons, or snaps, could be used for securing the waist band 30 around the subject's waist or to the subject's clothing could be used without departing from the spirit of the present disclosure.

The thigh band 34 is generally parallel to the waist band 30 and is sufficiently long to surround the subject's thigh. The thigh band 34 could be a continuous loop, but it is preferably in the form of a belt a belt for encircling the entire thigh of the subject, The thigh band 34 can be provided with a fastener 38 to make it easy for the subject to put the suspension system 14 on, and take it off. In the illustrated example, the fastener 38 includes an elongated band with mating fastener elements. The mating fastening elements 38 are preferably mating patches of a hook-and-loop style fastener, such as Velcro® fastener, to allow easy attachment and detachment. However, any conventional fasteners, such as buckles, buttons, or snaps, could be used for securing the thigh band 34 around the subject's thigh could be used without departing from the spirit of the present disclosure.

A pair of securing straps 42 is provided on the thigh band 34 adjacent to the extension strap 32. The securing straps 42 are positioned to engage an adjacent opening 28 at the top corners of the urine bag 18 to secure the urine bag 18 on the thigh band 34. It should be noted that while the securing straps 42 are shown to be provided on the thigh band 34 in the illustrated example, the securing straps 42 can be provided on the extension strap 32, instead of thigh band 34, as long as the securing straps 42 can be positioned to engage the adjacent openings 28 of the urine bag 18 to secure the urine bag 18 to the suspension system 14. Because the thigh band generally does not change in dimension, the corners of the bag 18 are held in a substantially fixed distance, preventing crushing of the bag, which could tend to apply a back pressure to the catheter.

The extension strap 32 extends perpendicularly from the waist band 30 a sufficient length so that when the waist band is secured at the subject's wait, the strap extends down along the side of the subject sufficiently such that the thigh band 34 can be attached to the thigh of the subject. A pair of fasteners 44 and 46 are disposed at the extension strap 32 for positioning and securing the catheter 16. The fasteners 44 and 46 are disposed adjacent to the outlet end 22 and below the branch 24. The branch 24 provides for attachment to a pump device, which can be used to inflate a balloon that may be disposed at the end of the catheter 16 for anchoring the catheter within the subject's urethra. The engagement between the fasteners 44 and the branch 24 resists movement of, the catheter 16 due to pulling of the bag from movement by the subject or from the increasing weight of urine that is collected in the bag. Therefore, the catheter 16 remains in a "slack" or "no tension" state despite the increased weight of the urine bag 18 and no pulling force is exerted on the urethra of the patient to cause pain. The fasteners 44 and 46 include fastening means, such as mating patches of a hook-and-loop style fastener, Velcro®, although some other type of fastening means could be used.

A panel 48 is provided at a lower end of the extension strap 32 to separate and insulate the patient's thigh from the urine bag 18. The panel 48 can be of any shape and size and does not have to be an integral part of the extension strap 32 as shown in the illustrated example, as long as the panel 48 provides proper separation between the urine bag 18 and the thigh to improve comfort. The panel 48 can be of sufficient size and length so that a second pair of securing straps or a second thigh band can be attached to the panel 48 to secure the lower end of the urine bag 18. Alternatively, the panel 48 can be in a form of a pouch to receive the urine bag 18 therein.

The waist band 30 and the extension strap 32 are preferably made of a washable, non-stretchable material so that the construction of the suspension system 14 is not distorted due to the increased weight of the urine bag 18.

With the construction of the present urine collection system 10, the urine collection device 12 can be easily disassembled from the suspension system 14 for cleaning or emptying purposes.

Figure 3:
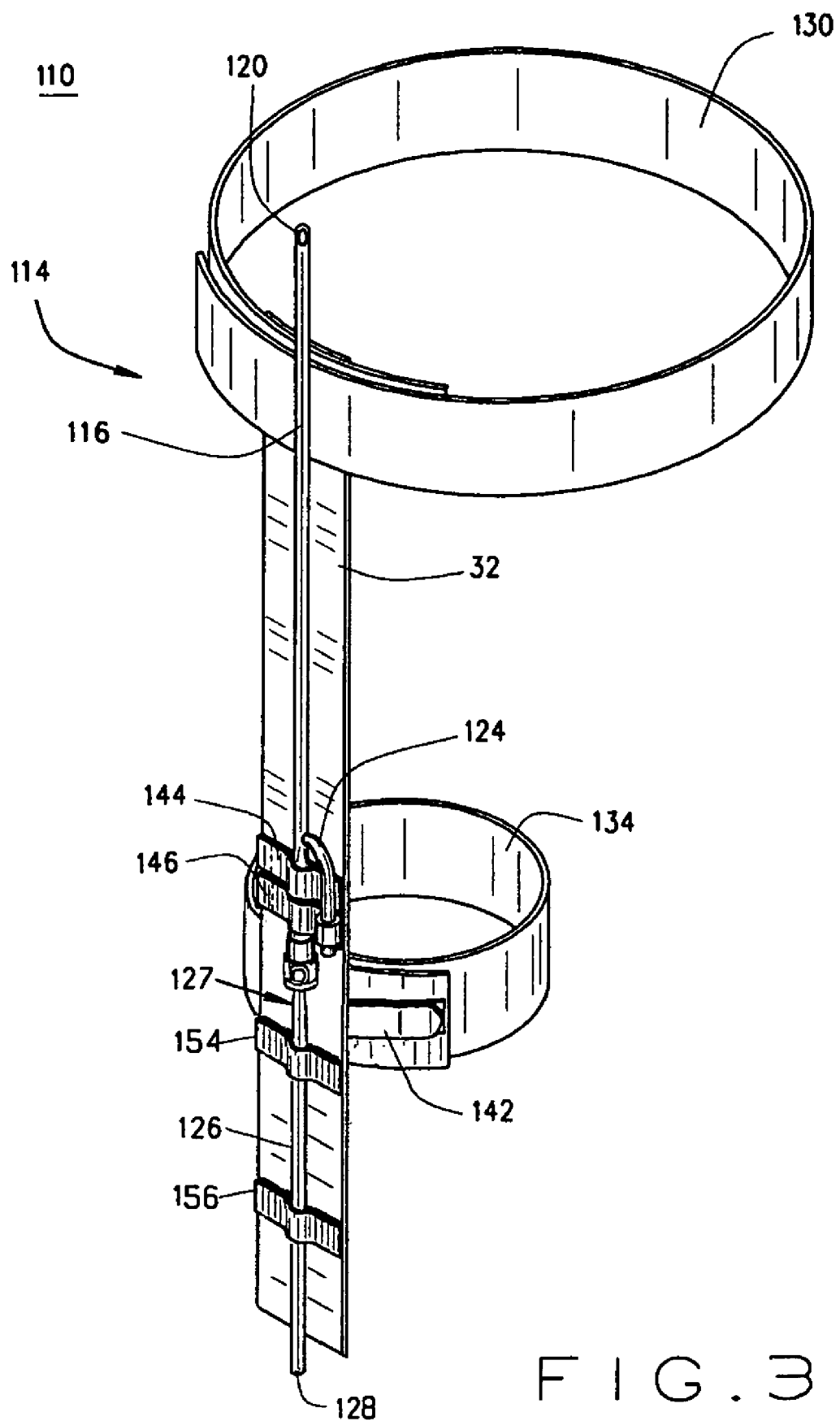
FIG. 3 is a perspective view of a second embodiment of a urine collection system in accordance with the teachings of the present disclosure.
Figure 4:
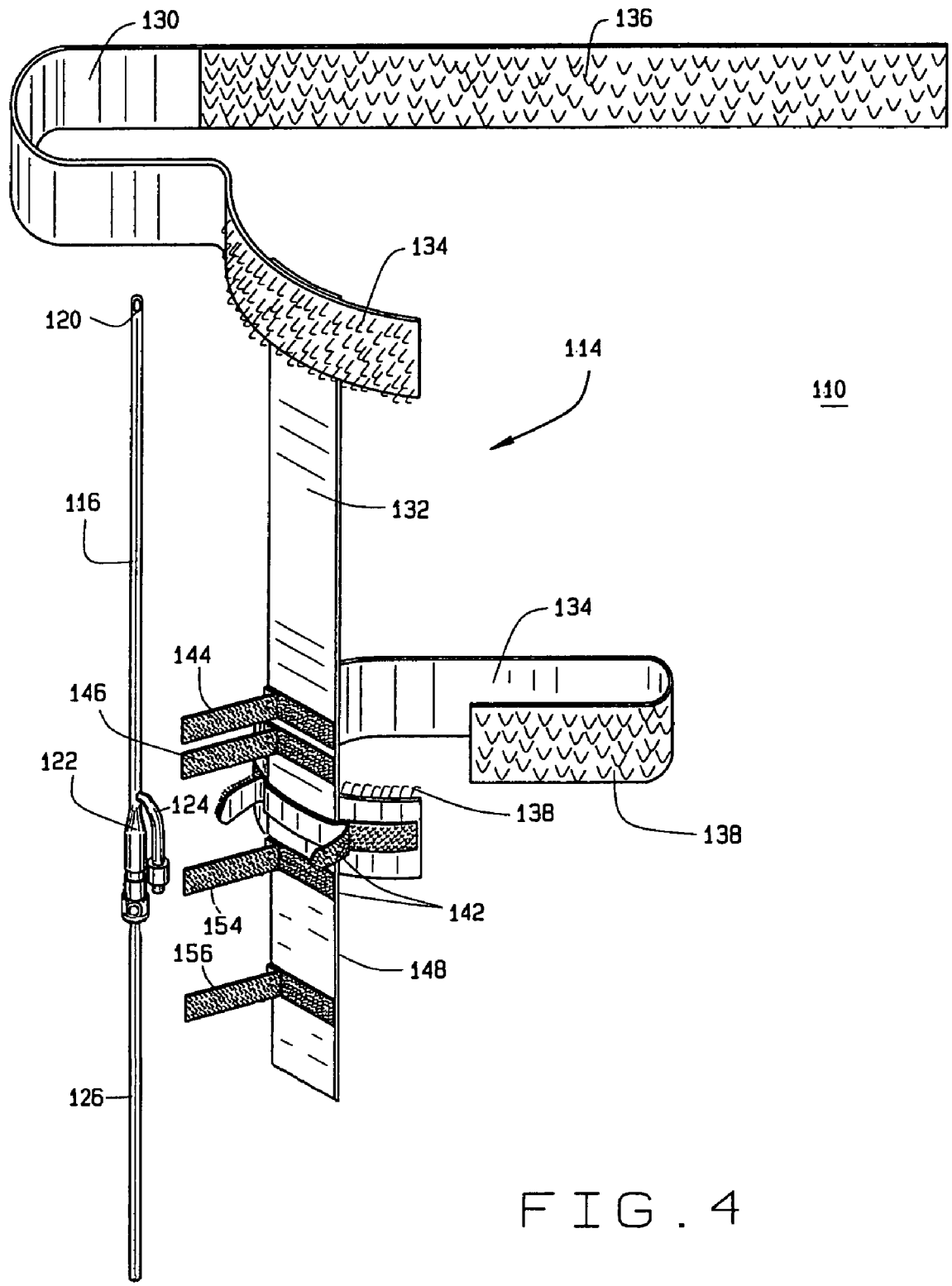
FIG. 4 is a perspective view of the urine collection system of FIG. 3, wherein the urine collection device is disassembled from a wearable suspension system therefore.

Referring to FIGS. 3 and 4, a second embodiment of a urine collection system in accordance with the teachings of the present disclosure is illustrated and generally indicated by reference numeral 110. The urine collection system 110 includes a catheter 116 and a wearable support or a wearable suspension system 114. The urine collection system further includes a length of tubing 126 that may be secured to the wearable support 114. The catheter 116 has an inlet end 120 for communicating with the urethra of the subject, and an outlet end 122 for engaging the inlet in the upper end 127 of the length of tubing 126.

The catheter 116 can be a Foley catheter, which is adapted to be inserted into the urethra of the patient, or a Texas catheter, which is to be connected to the penis of a male patient via a condom-like envelope, or any other type of internal or external urine collection catheter. In any case, the catheter 116 usually includes a branch 124 adjacent to the outlet end 122, the function of which will be described later.

The urine tubing 126 has a discharge outlet at its lower end for connection to a urine collection bag (not shown). In most applications the length of tubing 126 is mounted generally vertically, with the connection to the outlet end 122 of the catheter at the first inlet end of the tubing 127, and the discharge outlet 128 at the lower end. The urine tubing 126 preferably carries urine from the catheter to a urine collection bag that may be mounted to a stationary patient bed, or to a moveable support such as a stand on wheels. The urine collection apparatus worn by a patient provides for securing tubing of urine collection devices, and may be used with a large Foley catheter urine bag, or with a Suprapubic catheter or cystostomy catheter. Such a catheter is inserted in the lower abdomen above the pubic bone directly into the urinary bladder.

The suspension system 114 is used to support the urine collection components on the subject, and includes a waist band 130, an extension strap 132 depending from the waist band 130, and a thigh band 134 attached adjacent the free end of the extension strap 132. The waist band 130 could be a continuous loop, but it is preferably in the form of a belt for encircling the entire waist of the subject. The waist band 130 could also be in the form of a strip to be attached to a piece of clothing around the subject's waist without completely encircling the subject's waist. In either case, the waist band 30 can be provided with a fastener 136 to make it easy for the subject to put the suspension system 114 on, and take it off. In the illustrated example, the fastener 136 includes an elongated band with mating fastener elements. The mating fastening elements are preferably mating patches of a hook-and-loop style fastener, such as Velcro® fastener, to allow easy attachment and detachment. However, any conventional fasteners, such as buckles, buttons, or snaps, could be used for securing the waist band 130 around the subject's waist or to the subject's clothing could be used without departing from the spirit of the present disclosure.

The thigh band 134 is generally parallel to the waist band 130 and is sufficiently long to surround the subject's thigh. The thigh band 134 could be a continuous loop, but it is preferably in the form of a belt a belt for encircling the entire thigh of the subject, The thigh band 134 can be provided with a fastener 138 to make it easy for the subject to put the suspension system 114 on, and take it off. In the illustrated example, the fastener 138 includes an elongated band with mating fastener elements. The mating fastening elements 138 are preferably mating patches of a hook-and-loop style fastener, such as Velcro® fastener, to allow easy attachment and detachment. However, any conventional fasteners, such as buckles, buttons, or snaps, could be used for securing the thigh band 134 around the subject's thigh could be used without departing from the spirit of the present disclosure.

A pair of securing straps 142 is provided on the thigh band 134 adjacent to the extension strap 132. The securing straps 142 are adapted to engage an opening in the top corners of a urine bag where a urine bag may be used, to secure the urine bag on the thigh band 134. The extension strap 132 extends perpendicularly from the waist band 130 a sufficient length so that when the waist band is secured at the subject's wait, the strap extends down along the side of the subject sufficiently such that the thigh band 134 can be attached to the thigh of the subject. A pair of fasteners 144 and 146 are disposed at the extension strap 132 for positioning and securing the catheter 116. The fasteners 144 and 146 are disposed adjacent to the outlet end 122 and below the branch 124. The branch 124 provides for attachment to a pump device, which can be used to inflate a balloon that may be disposed at the end of the catheter 116 for anchoring the catheter within the subject's urethra. The engagement between the fasteners 144 and the branch 124 resists movement of the catheter 116 due to pulling of the portion of the urine carrying tubing 128 that is not secured to the support. Therefore, the catheter 116 remains in a "slack" or "no tension" state when the tubing 128 is accidentally or inadvertently pulled as a result of movement of the patient or the urine collection bag that is connected to the tubing 128. The fasteners 144 and 146 include fastening means, such as mating patches of a hook-and-loop style fastener, Velcro® although some other type of fastening means could be used.

A panel 148 is provided at a lower end of the extension strap 132 to secure the length of tubing 126 to the patient's leg. The panel 148 can be of any shape and size and does not have to be an integral part of the extension strap 132 as shown in the illustrated example, as long as the panel 148 provides proper separation between the length of urine tubing 126 and the thigh to improve comfort and provide support for the tubing 126. The panel 148 can be of sufficient size and length so that a second pair of securing straps 154 and 156 can be attached to the panel 148 to secure the lower end of the urine tubing 126. The second pair of securing straps 154 and 156 provide for supporting the length of tubing 126, such that movement of a urine collection bag in connection with the end 128 of the tubing 126 does not affect the catheter 116 or cause discomfort to the patient. Likewise, securing straps 154 and 156 sufficiently stabilize the tubing 126 to permit the patient to move relative to a urine collection bag attached to the end of the tubing 128, such that accidental entanglement of the tubing caused by the patient's movement does not result in a force applied to the catheter 116 or cause discomfort to the patient. In the embodiment illustrated in FIGS. 3 and 4, the panel 148 extends a minimum length of at least 4 inches to provide for at least one securing strap 156 spaced about three inches below the thigh band 134. A second thigh band (not shown) may also be attached to the panel 148 to secure the lower end of the panel 148 to the patient's leg, to further stabilize the panel and tubing 126.

Accordingly, the exemplary embodiment shown in the Figures provides a wearable support 110 for a urine collection catheter 116 engagingly receiving a length of collection tubing 126. The wearable support includes the waist band 130 that is adapted to be worn around the user's waist, an the extension strap 132 depending from the waist band 130. The thigh band 134 on the wearable support 110 is attached to the extension strap 132, and is adapted to be worn around the user's thigh. At least one fastener 146 on the extension strap 132 is included for engaging the catheter 116 to resist downward movement of the catheter 116 relative to the extension strap 132. At least one fastener 156 on the lower end portion of the extension strap is included for engaging and securing a portion of collection tubing 126, to resist movement of the collection tubing 126 such that movement of the catheter 116 relative to the extension strap 132 is resisted. The at least one fastener on the extension strap engages the catheter 116 below a branch 124 to resist downward motion of the catheter 116. The at least one fastener 156 on the lower end portion of the extension strap supports the collection tubing 126 in a manner that resists movement of the secured portion of tubing 126 and the catheter 116 relative to the extension strap 132, when an unsecured portion of the collection tubing 128 is being pulled. The thigh band 134 also supports the extension strap 132 in a manner that resists movement of the extension strap 132 relative to the patient when an unsecured portion of the collection tubing 128 is being pulled.

The waist band 130 and the extension strap 132 are preferably made of a washable, non-stretchable material so that the construction of the suspension system 114 is not significantly distorted by movement of the patient.

With the construction of the present urine collection system 110, the urine collection device 112 can be easily disassembled from the suspension system 114 for cleaning or emptying purposes.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A wearable support for a urine collection catheter comprising a catheter having an engaging outlet end for engagingly receiving a length of collection tubing, and a branch depending therefrom, the support comprising:
   a waist band adapted to be worn around the user's waist,
   an extension strap depending from the waist band,
   a thigh band attached to the extension strap, adapted to be worn around the user's thigh, the thigh band being positioned on the extension strap relative to the waist band so as to wrap around the thigh of a patient;
   a first fastener positioned on the extension strap above the thigh band, the first fastener being configured to engage the catheter below the branch only, to secure the catheter without securing the branch such that the first fastener resists downward movement of the catheter and provides for attachment of the branch to a pump device;

a second fastener positioned on the extension strap above the thigh band and below the first fastener, the second fastener being configured to engage the catheter above the outlet end and below the branch of the catheter; and at least one collection tubing securing strap on the lower end portion of the extension strap below the thigh band, for engaging and securing a portion of collection tubing to hold the portion of tubing secured to the catheter, to thereby resist movement of the collection tubing such that movement of the catheter relative to the extension strap is resisted;

whereby the wearable support is free of fasteners above the branch in the catheter, such that disengaging the first and second fasteners positioned below the branch provides for disassembly of the wearable support from the catheter for cleaning purposes.

2. The wearable support according to claim 1, wherein the catheter branch comprises a conduit that depends from the catheter and extends downward to a free end having an opening therein, and wherein the first fastener on the extension strap engages the catheter below the branch to resist downward motion of the catheter.

3. The wearable support according to claim 2 wherein the unsecured portion of the collection tubing extends to a collection device that is separate from the wearer of the wearable support.

4. The wearable support according to claim 3 wherein the unsecured portion of the collection tubing extends to a collection device that is separate from the wearer of the wearable support.

5. The wearable support according to claim 1, wherein the at least one collection tubing securing strap on the lower end portion of the extension strap supports the collection tubing in a manner that resists movement of the secured portion of tubing and the catheter relative to the extension strap when an unsecured portion of the collection tubing is being pulled.

6. The wearable support according to claim 1, wherein the thigh band supports the extension strap in a manner that resists movement of the extension strap relative to the patient when an unsecured portion of the collection tubing is being pulled.

7. The wearable support according to claim 1, wherein the unsecured portion of collection tubing comprises a free end portion of the collection tubing that extends beyond the fasteners on the lower panel.

8. The wearable support according to claim 1, wherein the at least one collection tubing strap on a lower portion of the extension strap secures the collection tubing in a generally vertical position, so as to resist downward movement of the catheter relative to the wearable support strap when an unsecured portion of the collection tubing is being pulled.

9. A wearable support for a urine collection catheter having an engaging outlet end for engagingly receiving a length of collection tubing, and a branch depending therefrom, the support comprising:

a waist band adapted to be worn around the user's waist;

an extension strap depending from the waist band;

a catheter having an outlet end configured to attach to a length of collection tubing, and a branch depending therefrom that provides for attachment of a pump device thereto;

a thigh band attached to the extension strap, the thigh band being positioned on the extension strap relative to the waist band such that the thigh band is adapted to be worn around the user's thigh; a first fastener positioned on the extension strap above the thigh band, the first fastener being configured to engage the catheter below the branch only, to secure the catheter without securing the branch such that the first fastener resists downward movement of the catheter and provides for attachment of the branch to a pump device;

a second fastener positioned on the extension strap above the thigh band and below the first fastener, the second fastener being configured to engage the catheter above the outlet end and below the branch of the catheter;

a length of collection tubing that extends at least the length of the extension strap and is engagingly received on the catheter, where the collection tubing includes an end portion that extends below the extension strap and is not secured to the wearable support;

at least two collection tubing securing straps on a lower portion of the extension strap below the thigh band for securing a portion of the collection tubing extending from the catheter to hold the portion of tubing secured to the catheter, to thereby support the secured portion of collection tubing in a manner that resists movement of the secured portion of tubing and catheter relative to the extension strap; and whereby the wearable support is free of fasteners above the branch in the catheter, such that disengaging the first and second fasteners positioned below the branch provides for disassembly of the wearable support from the catheter for cleaning purposes.

10. The wearable support according to claim 9 wherein the unsecured portion of the collection tubing extends to a collection device that is separate from the wearer of the wearable support.

11. The wearable support according to claim 10, wherein the first and second fasteners on the extension strap engage a lower portion of the catheter below the branch in such a manner that the branch is not restricted and the first and second fasteners below the branch resists downward movement of the catheter relative to the extension strap of the wearable support.

12. The wearable support according to claim 9, wherein the at least two collection tubing securing straps on a lower portion of the extension strap secures the collection tubing in a generally vertical position, so as to resist downward movement of the catheter relative to the wearable support strap when an unsecured portion of the collection tubing is being pulled.

* * * * *